United States Patent

Gross et al.

[11] Patent Number: 5,908,450
[45] Date of Patent: Jun. 1, 1999

[54] PHYSIOLOGIC MITRAL VALVE IMPLANTATION HOLDING SYSTEM

[75] Inventors: Jeffrey M. Gross; Mark C. S. Shu, both of Mission Viejo; Luis A. Salazar, Chino Hills, all of Calif.

[73] Assignee: Medtronic, Inc., Minneapolis, Minn.

[21] Appl. No.: 08/808,553

[22] Filed: Feb. 28, 1997

[51] Int. Cl.⁶ .................................................. A61F 2/24
[52] U.S. Cl. ............................................................ 623/2
[58] Field of Search ................................... 623/2, 900

[56] References Cited

FOREIGN PATENT DOCUMENTS

3614292  11/1987  Germany ............................ 623/2

Primary Examiner—David H. Willse
Attorney, Agent, or Firm—Harry G. Weissenberger

[57] ABSTRACT

A temporary holder for a physiologic mitral valve includes a structure which releasably clamps the annulus of the valve between the rim of a plate and a snap ring. The structure also includes a pair of papillary head holders which hold the papillary heads of the valve at a predetermined distance and angle from the annulus plate for optimum surgical positioning. The papillary heads are temporarily sutured to their holders and can be released by a simple scalpel stroke.

15 Claims, 9 Drawing Sheets

PHYSIOLOGIC MITRAL VALVE IMPLANTATION HOLDING SYSTEM

FIELD OF THE INVENTION

This invention relates to the implantation of physiological mitral valves in the human heart, and more particularly to a holding system for holding the valve in a proper position during the implantation surgery.

BACKGROUND OF THE INVENTION

U.S. Pat. No. 5,662,704 issued Sep. 2, 1997 and entitled "Physiological Mitral Valve Bioprosthesis" describes the selection, preparation and positioning of a xenograft such as a porcine mitral valve for valve replacement surgery in the human heart.

As will be readily appreciated from that discussion, the orientation of the annulus and papillary heads of a xenograft mitral valve is three-dimensional in nature. This also holds true for a stentless physiological mitral valve (PMV). Both the PMV's annulus and papillary heads are free to distort when the valve is held in one's hand or when the valve is implanted in the mitral position of a recipient. If the valve is implanted in a distorted geometry, both hemodynamic performance and long term durability could suffer. It is therefore desirable to hold the prosthesis temporarily in its optimum geometric configuration so that the valve may be implanted properly. Once the valve's implantation orientation is set relative to the patient's left ventricular geometry, the temporary holder is removed. The implantation position of the valve in the left ventricle then provides the necessary rigidity and structure for valve function.

Temporary holding systems for holding implants have previously been used in annuloplasty. They have not, however, been used in stentless mitral xenografts because that type of surgery poses more complex problems than does annuloplasty. Consequently, a need exists for a temporary holder system suitable for the placing of non-stented chordally supported mitral xenograft valves, or pericardial and synthetic derivatives of the natural mitral valve in which temporary geometric positioning is necessary to facilitate implantation.

SUMMARY OF THE INVENTION

The invention fills the above-described need by providing a holding system composed of three components: an inner annulus holder, an outer annulus clamp, and papillary head holders. The inner annulus holder and outer annulus clamp form the mechanism to hold the valve annulus while the papillary head holders fix the valve's papillary heads in a rigid anatomic geometry relative to the valve's annulus. Preferably, the holding system of this invention is constructed of a clear plastic such that the valve's inflow annulus and any positioning markers thereon may be clearly seen when the valve is mounted on the holder.

DESCRIPTION OF THE PREFERRED EMBODIMENT

Figure 1:
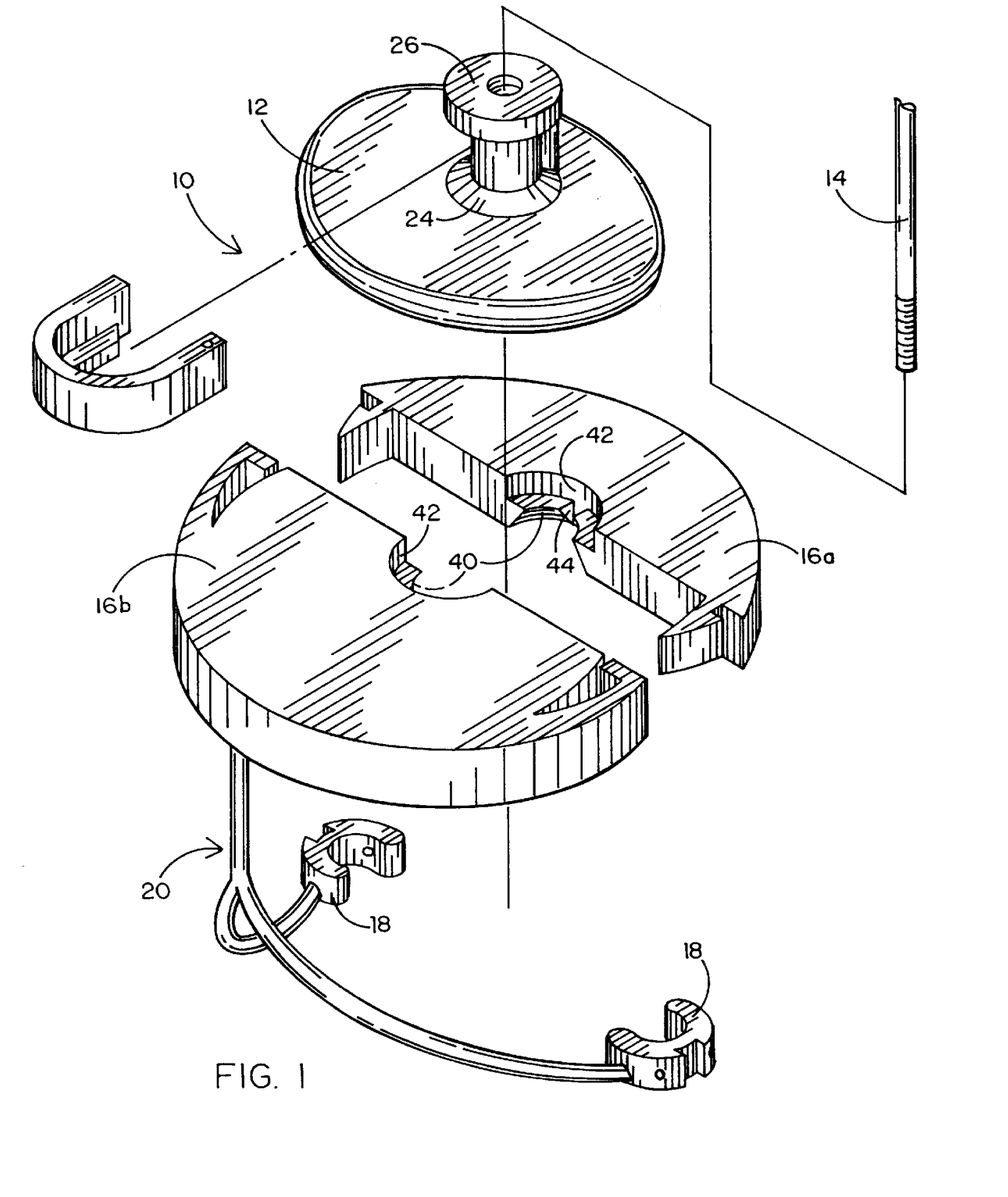
FIG. 1 is an exploded perspective view of the holding system of this invention.

In the exploded view of FIG. 1, the holding system 10 of this invention is seen to consist of an inner annulus holder 12 with a detachable obturator handle 14, an outer annulus clamping assembly 16 composed of an anterior clamp 16a and a posterior clamp 16b, and a pair of papillary head holders 18, spaced from each other and from the posterior clamp 16b by a support structure 20.

Figure 2A:
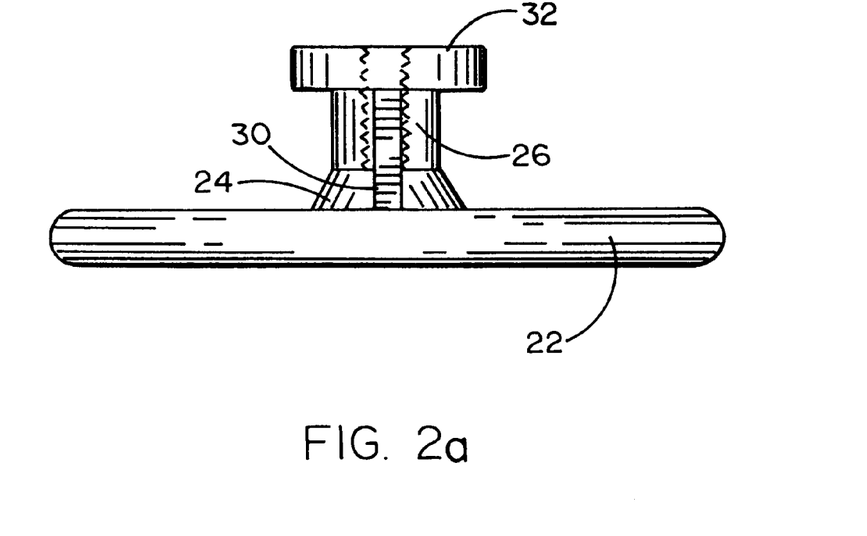
FIGS. 2a and 2b are side and plan views, respectively, of the inner annulus holder.
Figure 2B:
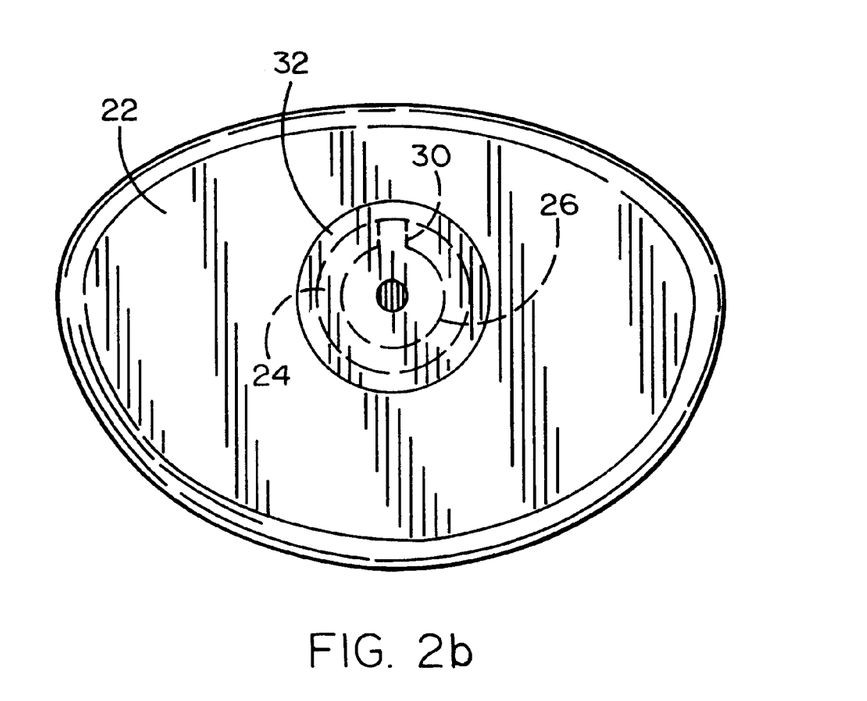
Figure 6:
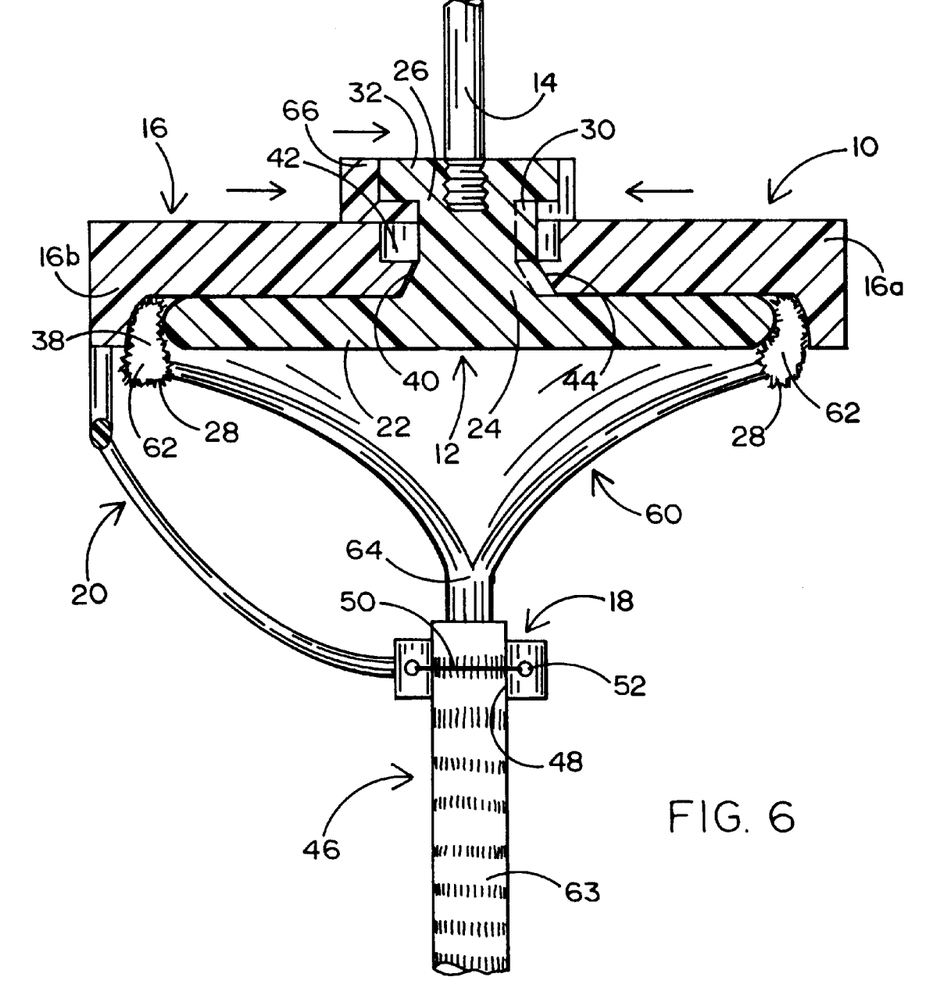
FIG. 6 is a vertical section illustrating the positioning of the valve on the holder in the clamping position.
Figure 7:
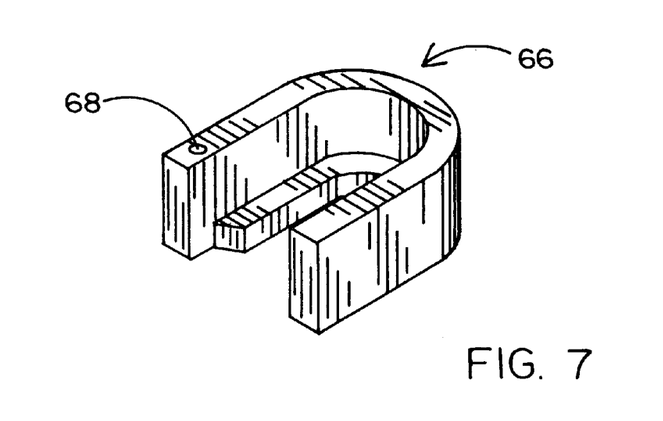
FIG. 7 is a perspective view of the locking key.
Figure 8:
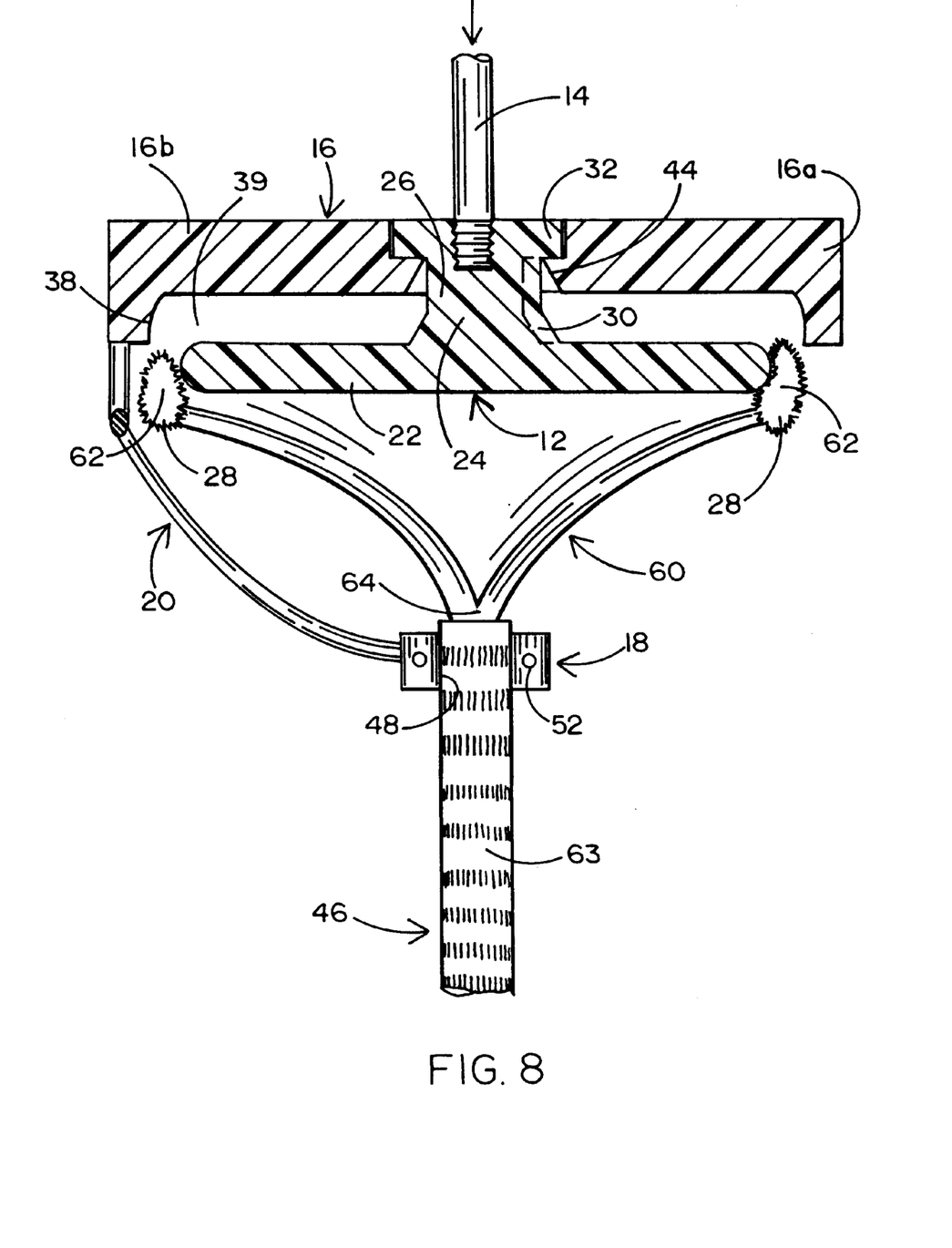
FIG. 8 is a vertical section similar to FIG. 6 but showing the holder in the release position.

The inner annulus holder 12 is depicted in more detail in FIGS. 2a and 2b. It consists essentially of a plate 22 which is attached through a tapered release shaft 24 to a threaded handle socket 26. The plate 22 is shaped and dimensioned to contact the inner diameter of the PMV's annulus at the band formed by the PMV's annular sewing cuff 28 (FIG. 6). The plate 22 thus provides a form for the PMV's annular inside diameter against which the annulus can be clamped in order to hold the annulus in place during implantation. The PMV should require slight stretching to fit over the inner annulus holder in order to facilitate mounting. The edges of the plate 22 are rounded to prevent tissue damage, and the shape of the plate 22 is so chosen as to approximate the shape of the mitral annulus during end systole. An alignment tab 30 is formed on the release shaft 24 to assure proper alignment of the holder 12 with the clamping assembly 16. The handle socket 26 carries at its top an annular flange 32 for a purpose described below.

Figure 3A:
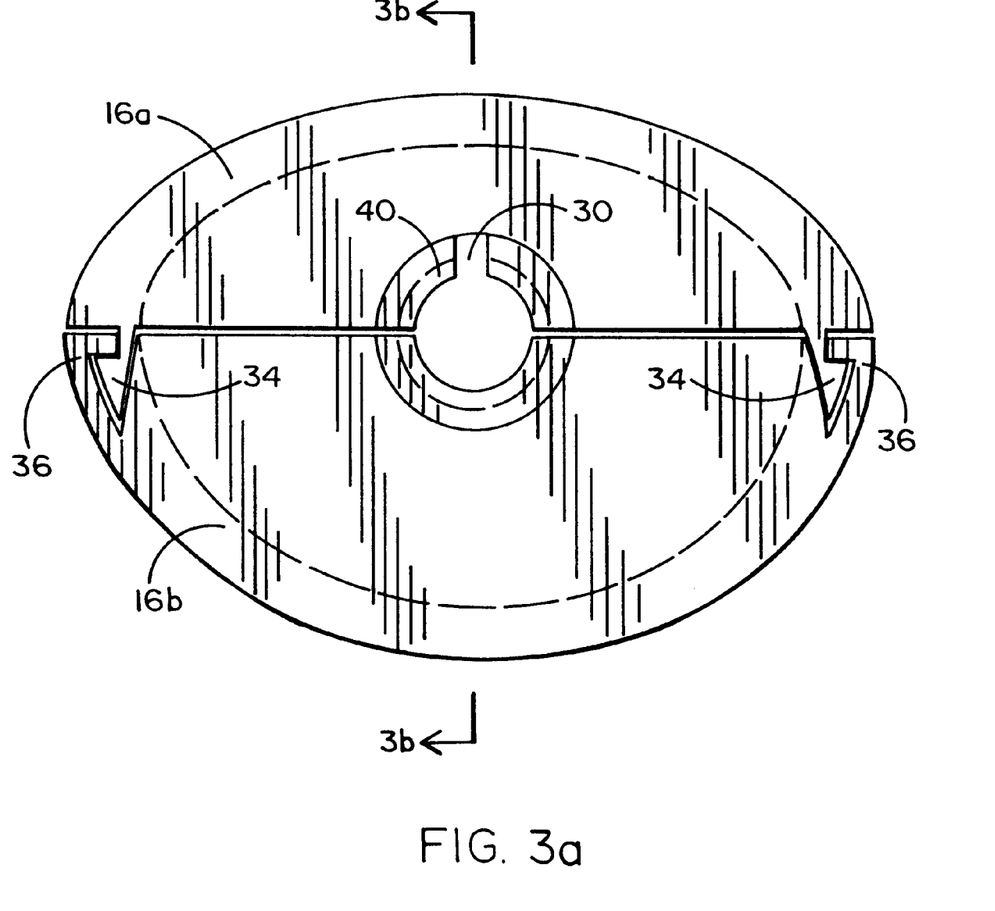
FIGS. 3a and 3b are a plan view and a section along line 3b—3b, respectively, of the outer annulus clamp.
Figure 3B:
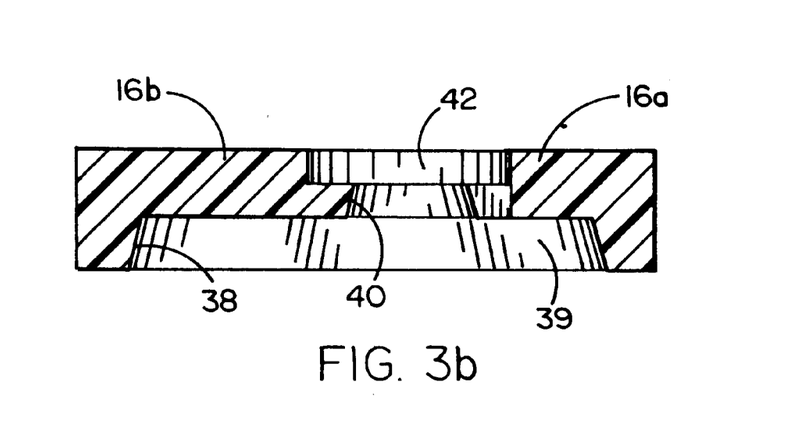

FIGS. 3a and 3b show the arrangement of the clamping assembly 16. The anterior clamp 16a and the posterior clamp 16b can be mated around the shaft 24 of the interior annulus holder 12 in the manner of a snap ring by horizontally engaging the hooks 34 of the anterior clamp 16a with the resilient shoulders 36 formed on the posterior clamp 16b. When the clamps 16a and 16b are mated, the tapered wall 38 defines a recess 39 of the same shape as, but slightly larger than, the plate 22 of the holder 12. The face 40 engages and matches the shaft 24 of holder 12, and the recess 42 is shaped and dimensioned to receive the flange 32 of the handle socket 26 during the release operation described below. An alignment slot 44 in the face 40 cooperates with the alignment tab 30 of the holder 12 to assure proper alignment of the holder 12 with the clamp 16.

Figure 4A:
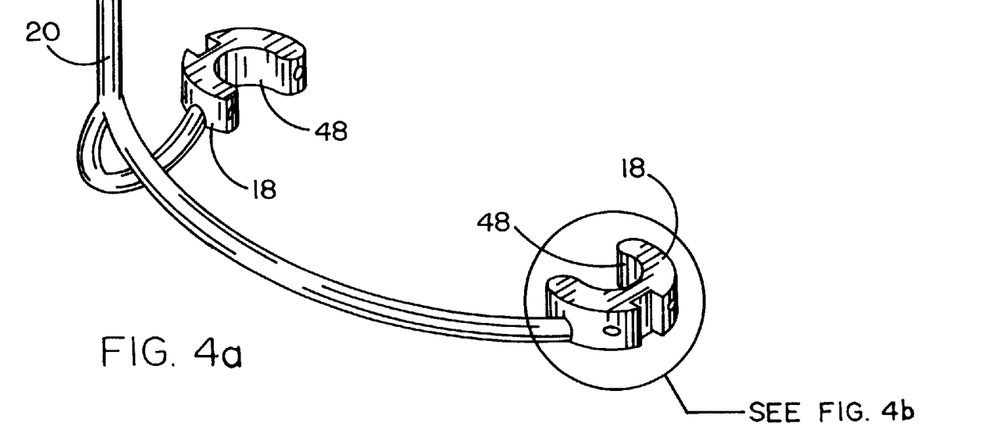
FIGS. 4a, 4b and 4c are a general perspective view, an enlarged perspective view, and a rear perspective view, respectively, of the papillary head holders.
Figure 4B:
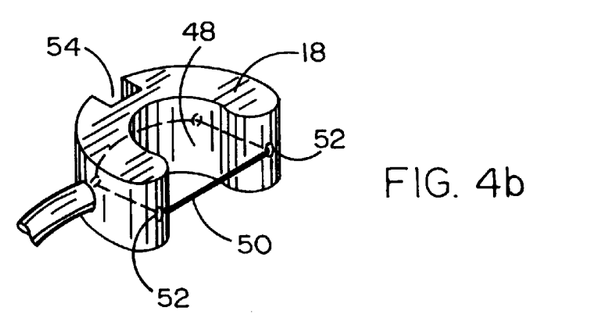
Figure 4C:
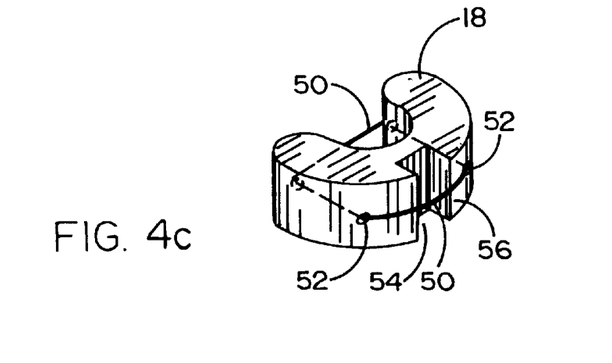

The papillary head holders 18 are illustrated in FIGS. 4a–c. As shown in FIG. 4a, the holders 18 are suspended from the posterior clamp 16b by the support structure 20 which orients them to properly position the papillary heads 46 when the PMV is mounted on the holding system 10. The holders 18, as illustrated in more detail in FIGS. 4b and 4c, have a generally curved face 48 which serves as a form for engaging the papillary heads 46. The papillary heads 46 are held against the face 48 by sutures 50, bands or other holding elements which may pass through openings 52 and may be tied at the rear of the holders 18. A scalpel groove 54 may be provided in the rear face 56 of holders 18 to facilitate cutting the suture 50 when releasing the papillary heads 46 after implantation.

Figure 5:
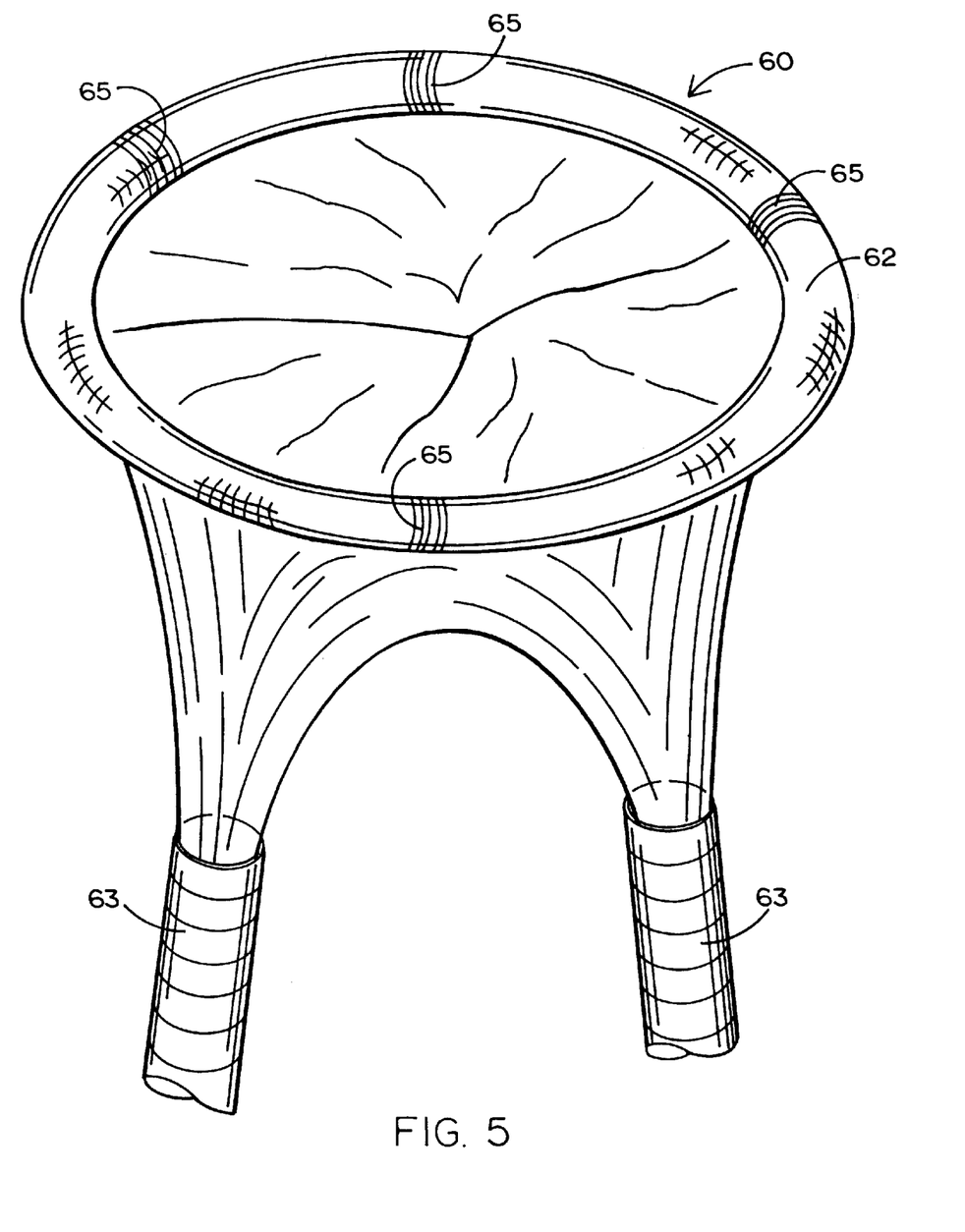
FIG. 5 is a perspective view of a physiologic mitral valve xenograft.

The use of the above-described apparatus is illustrated in FIGS. 5–8. As disclosed in more detail in U.S. Pat. No. 5,662,704, FIG. 5 shows a xenograft mitral valve 60 prepared for implantation. The annulus 62 of the valve has been covered with a cloth sewing cuff 28 which facilitates the suturing of the annulus 62 to the host's mitral annulus. The sewing cuff 28 also carries colored markers 65 (which can be clearly seen through the clear plastic of the holding system 10) to identify the valve's commisures and short axis for proper placement of the surgical sutures. Sewing tubes 63 have also been attached to the papillary heads 46 at the depending chordae tendinae 64 to lengthen them and facilitate their suturing, as the chordae tendinae of a xenograft are typically too short to reach their anchor points in the human heart.

The exact three-dimensional positioning of the papillary heads 46 with respect to the annulus 62 at implant is critical to the efficiency and long-term success of the implant by minimizing stresses on the chordae tendonae 64 during the beating of the heart. Consequently, a unique geometry, in terms of length and angular position from the annulus 62, is required for the papillary head holders 18 on each side of the PMV.

As shown in the vertical section of FIG. 6, the sewing cuff 28 of the annulus 62 is first slipped onto the plate 22 in such a way that only the sewing cuff 28 is in contact with the plate 22. The annulus 62 is so oriented that the anterior and posterior clamps 16a and 16b correspond with the anterior and posterior leaflets of the PMV 60. The annulus 62 is then clamped to the plate 22 by mating the clamps 16a and 16b around the plate 22. The plate 22 is held in the clamping recess 39 by slipping a U-shaped locking key 66 (FIG. 7) under the flange 32 of the handle socket 26. The locking key 66 is preferably secured to the clamping assembly 16 by a pin or other fastening device (not shown) to avoid its accidental placement in the operating field. The space between the plate 22 and the tapered wall 38 is such that the clamp 16 exerts a clamping force against the plate 22 which is sufficient to firmly hold the annulus 62 without damaging it by abrasion or crushing of tissue. The chordae tendinae 64 are next sutured to the papillary head holders 18 just above the sewing tubes 63, leaving the sewing tubes 63 free for trimming and suturing. Finally, the obturator handle 14 is attached to the socket 26.

The holding system is now ready for placement of the valve 60 into its implant position. Although implantation methods may vary depending upon the surgeon's preference, a typical implantation may proceed as follows:

1) The mitral valve is exposed using standard left atriotomy techniques as understood by those versed in the art. Stay sutures are placed in the mitral annulus at the trigones and the short axis of the native valve.

2) The native valve is excised leaving the papillary heads intact. The native chordae tendinae are trimmed close to the native papillary heads.

3) Based on the geometry of the PMV 60 and that of the native left ventricle, the distance between the native annulus and the site of attachment for the PMV papillary heads is determined through measurement. The PMV sewing tubes 63 are cut to reflect this length such that the total length from the PMV's annulus 62 to the end of the PMV's sewing tube 63 is identical to that measured. (The measurement of the annulus to papillary head attachment point length can also be determined preoperatively using echo Doppler techniques).

4) Three or more plegetted sutures are made in the native left ventricle at the point of attachment for the PMV papillary head sewing tubes 63.

5) The PMV 60 on the holder 10 is held by the handle 14 over and normal to the native annulus such that the annulus markers 61 on the PMV sewing cuff 28 align with the stay sutures placed in the native annulus. The annulus 62 of the PMV 20 and the native annulus are parallel.

6) The plegetted sutures thus placed are run up to the PMV's papillary sewing tubes 63, carefully maintaining orientation and avoiding twisting of the PMV papillary head 46 by misorientation of the plegetted sutures onto the PMV's sewing tube 62.

7) The valve 60 is released from the holder by first releasing the papillary heads from their holders 18. This is done by running a scalpel along the scalpel groove 54. The PMV's annulus 62 is then released by sliding out the locking key 66 and pushing the inner annulus holder 12 downward until the flange 32 seats in the recess 42. This releases the clamping pressure on the annulus 62.

8) With the valve 60 released from the holder 10, the PMV's papillary sewing tubes 63 are slid down along their suture lines to their seating location in the left ventricle and tied off. The holder 10 is discarded. While the PMV's sewing tubes 63 are being tied down, the annulus 62 is pushed out of the way in the left ventricle to facilitate tying off of the PMV's papillary head sewing tubes 63.

9) The PMV's annulus 62 is brought back up to the patient's annulus and aligned such that the colored markers 65 of the PMV's annulus 62 coincide with the stay sutures of the patient's annulus. This insures annular alignment.

10) The PMV's annulus is then sewn in, using either continuous or interrupted sutures.

11) The valve 60 is checked for competency and prolapse. Suture adjustments may be made as necessary to insure that there is no paravalvular leakage and proper coaptation of the leaflets.

12) The remainder of the operation is conducted in a manner similar to that of a standard mitral valve replacement procedure as understood by those skilled in the art.

Figure 9:
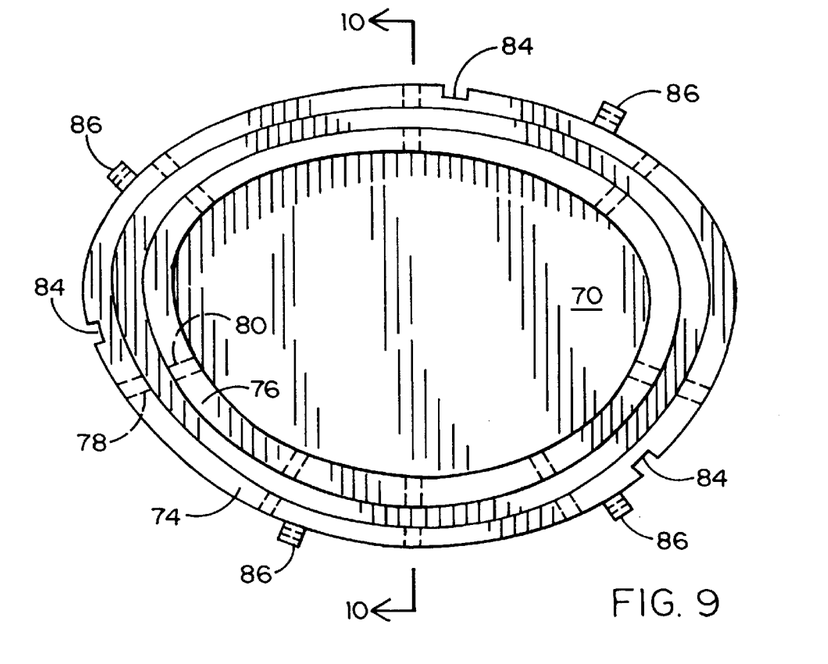
FIG. 9 is a bottom plan view of an alternative embodiment of the invention.
Figure 10:
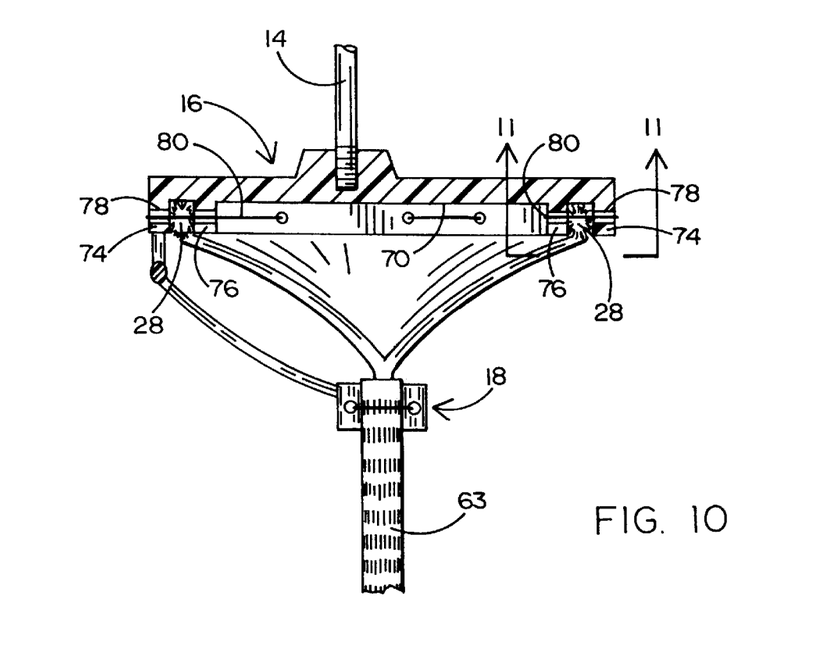
FIG. 10 is a vertical section along line 10—10 of FIG. 9.
Figure 11:
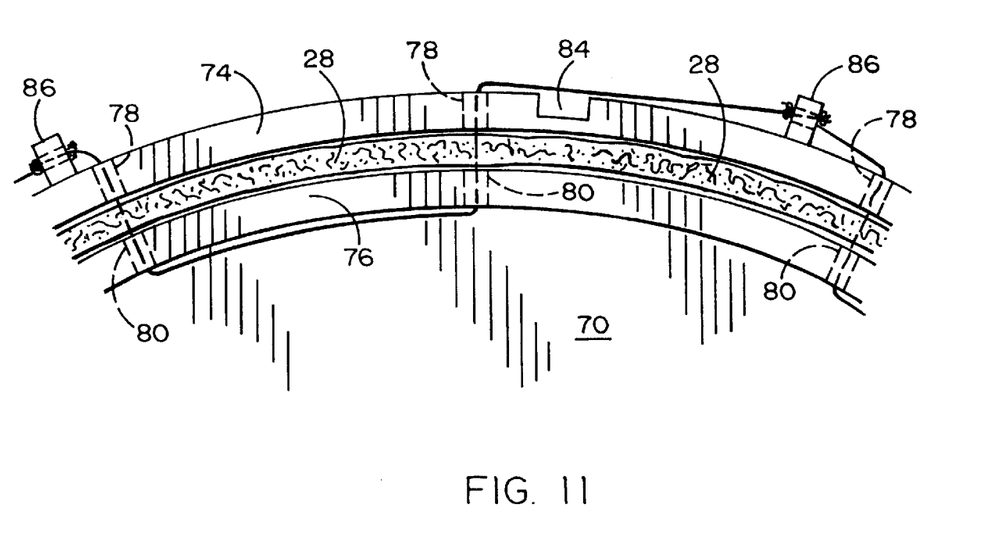
FIG. 11 is a fragmentary enlarged bottom view along line 11—11 of FIG. 10.

An alternative preferred embodiment of the invention is illustrated in FIGS. 9 through 11. In the plan view of FIG. 9, the supporting member 70 is shown to have the general shape of a mitral valve annulus. On its upper side (FIG. 10), the supporting member 70 carries a handle socket 72 which receives the obturator handle 14 (FIG. 1). On the underside, the supporting member 70 has a pair of generally concentric flanges 74, 76 depending therefrom.

Each of the flanges 74, 76 has small transverse openings 78, 80 formed therein at intervals along its curcumference. Each opening 78 (typically three along the anterior annulus and five along the posterior annulus a right parenthesis in the outer flange 74 is circumferentially aligned with a corresponding opening 80 in the inner flange 76, for a purpose best illustrated in FIG. 11. In FIGS. 10 and 11, the sewing cuff 28 is shown inserted into the space between the flanges 74, 76 and sewn in its upper half to supporting member 70 by sutures 82.

A preferred layout of the sutures 82 is shown in FIG. 11. The positioning of sutures 82 shown in that figure makes it possible, after the lower half of the sewing cuff has been sewn to the patient's mitral valve annulus, to release the support member 70 from the sewing cuff 28 by a scalpel cut at, e.g., recess 84. Each of the sutures 82 is preferably tied on each side of an apertured protrusion 86 so as to remain attached to the protrusion 86 after being cut at 84 and pulled out of the sewing cuff 28.

It should be understood that the exemplary physiologic mitral valve implantation holding system described herein and shown in the drawings represents only presently preferred embodiment of the invention. Indeed, various modifications and additions may be made to such embodiments without departing from the spirit and scope of the invention. Thus, other modifications and additions may be obvious to those skilled in the art and may be implemented to adapt the present invention to a variety of different applications.

We claim:

1. A temporary holding system for physiologic mitral valves, comprising:
   a) a support member adapted to supportingly receive the annulus of a physiologic mitral valve having an annulus and papillary heads; and
   b) a pair of papillary head holders rigidly positioned with respect to said support member and adapted to have said papillary heads of said valve temporarily attached thereto.

2. The system of claim 1, in which said support member includes:
   i) a plate member having a rim and including a plate adapted to receive around said rim said annulus of said physiologic mitral valve; and
   ii) a retaining member adapted to be positioned around said rim to releasably retain said annulus on said rim without damage to said annulus.

3. The system of claim 1, in which said support member includes a plate member with substantially parallel concentric depending circumferential flanges adapted to receive said annulus therebetween, said flanges having transverse openings therein adapted to allow the passage of sutures for releasably securing said annulus to said plate member.

4. The system of claim 2, in which said retaining member includes a plurality of coplanar interengageable clamps each surrounding a portion of said rim.

5. The system of claim 2, in which said rim is rounded in cross section.

6. The system of claim 1, in which said papillary head holders are arranged to each have a papillary head temporarily secured thereto by a holding element.

7. The system of claim 6, in which said holding element is a suture.

8. The system of claim 7, in which said holders each have a scalpel groove on their back side, said holding element extending across said groove for easy severing of said suture to release said papillary head from said holder.

9. A temporary holding system for physiologic mitral valves, comprising:
   a) a support member adapted to supportingly receive the annulus of a physiologic mitral valve having an annulus and papillary heads; and
   b) a pair of papillary head holders rigidly positioned with respect to said support member and adapted to have said papillary heads of said valve temporarily attached thereto;
   c) said support member including:
      i) a plate member having a rim and including a plate adapted to receive around said rim said annulus of said physiologic mitral valve; and
      ii) a retaining member adapted to be positioned around said rim to releasably retain said annulus on said rim without damage to said annulus; and
      iii) said retaining member including a plurality of coplanar interengageable clamps each surrounding a portion of said rim.

10. The system of claim 9, in which said clamps are interengageable in the form of a snap ring.

11. The system of claim 10, in which said annulus can be released from said clamping member after the interengagement of said clamps by moving said plate member downwardly from the plane of said retaining member.

12. The system of claim 11, further comprising a releasable locking key arranged to engage said plate member and said retaining member to prevent said downward movement of said retaining member with respect to said plate.

13. A temporary holding system for physiologic mitral valves, comprising:
   a) a support member adapted to supportingly receive the annulus of a physiologic mitral valve having an annulus and papillary heads; and
   b) a pair of papillary head holders rigidly positioned with respect to said support member and adapted to have said papillary heads of said valve temporarily attached thereto;
   c) said support member including:
      i) a plate member having a rim and including a plate adapted to receive around said rim said annulus of said physiologic mitral valve; and
      ii) a retaining member adapted to be positioned around said rim to releasably retain said annulus on said rim without damage to said annulus;
      iii) said retaining member having a wall arranged to clamp said annulus, said wall being downwardly outwardly tapered.

14. A temporary holding system for physiologic mitral valves, comprising:
   a) a support member adapted to supportingly receive the annulus of a physiologic mitral valve having an annulus and papillary heads;
   b) a pair of papillary head holders rigidly positioned with respect to said support member and adapted to have said papillary heads of said valve temporarily attached thereto;
   c) said support member including:
      i) a plate member having a rim and including a plate adapted to receive around said rim said annulus of said physiologic mitral valve; and
      ii) a retaining member adapted to be positioned around said rim to releasably retain said annulus on said rim without damage to said annulus; and
   d) said support member being transparent to allow observation of positioning markings on said annulus.

15. A temporary holding system for physiologic mitral valves, comprising:
   a) a support member adapted to supportingly receive the annulus of a physiologic mitral valve having an annulus and papillary heads;

b) a pair of papillary head holders rigidly positioned with respect to said support member and adapted to have said papillary heads of said valve temporarily attached thereto;

c) said support member including a plate member with substantially parallel depending circumferential and substantially concentric inner and outer flanges adapted to receive said annulus therebetween, said flanges having transverse openings therein circumferentially aligned with one another and adapted to allow the passage of sutures for releasably securing said annulus to said plate member.

* * * * *